United States Patent [19]

Nakamura et al.

[11] Patent Number: 4,678,921
[45] Date of Patent: Jul. 7, 1987

[54] PHOTO-ELECTRIC SMOKE DETECTOR WITH LIGHT SHIELDING ELECTRODE

[75] Inventors: Takehiro Nakamura, Nishio; Susumu Sato, Okazaki; Tadashi Hattori, Okazaki; Teiichi Nabeta, Okazaki; Minoru Kato, Ichinomiya, all of Japan

[73] Assignees: Nippondenso Co., Ltd., Kariya; Nippon Soken, Inc., Nishio, both of Japan

[21] Appl. No.: 700,383

[22] Filed: Feb. 11, 1985

[30] Foreign Application Priority Data

Feb. 13, 1984 [JP] Japan .................................. 59-25357

[51] Int. Cl.$^4$ ............................................ G01N 15/06
[52] U.S. Cl. .................................. 250/574; 250/211 J; 250/237 R

[58] Field of Search ................ 250/216, 211 R, 211 J, 250/211 K, 237 R, 573, 574, 575; 357/4; 340/630; 356/438, 439, 337

[56] References Cited

U.S. PATENT DOCUMENTS 3,600,588  8/1981  Sayce ............................... 250/211 R
4,242,673  12/1980  Cooper ................................ 250/574

Primary Examiner—David C. Nelms
Attorney, Agent, or Firm—Cushman, Darby & Cushman

[57] ABSTRACT

In a photo-electric smoke detector device, a first photo-detector receives the light emitted from a light emitter and scattered by smoke, and a second photo-detector directly receives the light emitted from the light emitter. The second photo-detector has an element surface on which trimmed electrodes are arranged. The electrodes of the second detector act to limit the amount of light emitted from the light emitter and transmitted to the elements of the second detector.

8 Claims, 12 Drawing Figures

PHOTO-ELECTRIC SMOKE DETECTOR WITH LIGHT SHIELDING ELECTRODE

BACKGROUND OF THE INVENTION

The present invention relates to a photo-electric smoke detector.

In a conventional method of compensating for the smear caused by the dust or nicotine attached on the surface of a light emitter or a photo-detector or the deterioration of the light emitter of a photo-electric smoke detector, a photo-detector for receiving direct light and a photo-detector for receiving scattered light are provided and set to the same output level under a predetermined condition. In this method of setting, the gain of the amplifiers connected to the photo-detectors is regulated.

SUMMARY OF THE INVENTION

The object of the present invention is to provide a smoke detector in which the amount of light received by a pair of photo-detectors, but not the gain of amplifiers is regulated, and the secular variations of the operation of regulating the amount of light are minimized.

DESCRIPTION OF THE PREFERRED EMBODIMENTS

Figure 1:
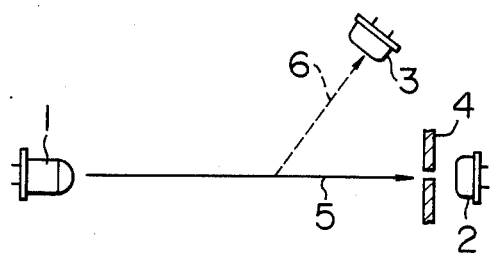
FIG. 1 is a diagram for explaining a basic configuration of the present invention.

A basic configuration of the present invention is shown in FIG. 1. Reference numeral 1 designates a light source made up of a light-emitting diode, numeral 2 a photo-detector for receiving direct light made of PIN-type Si photo-diode, and numeral 3 a photo-detector for receiving scattered light. A slit 4 is arranged before the photo-detector 2 to regulate the amount of light entering the photo-detector 2.

Figure 3:
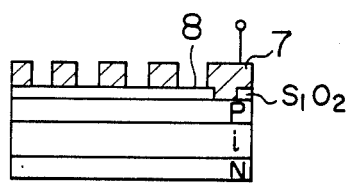

That part of the light radiated from the light-emitting diode 1 which enters the photo-detector 3 is very small in amount. Therefore, in order to keep the output of the photo-detector 3 equal to that of the photo-detector 2, the width of the slit 4 must be reduced greatly. According to the present invention, this problem is solved by using a Si photo-diode having a front light-receiving surface of a pattern as shown in the plan view in the drawing as the photo-detector 2. Specifically, the photo-detector 2 is so constructed that a metal member 7 (aluminum or gold) functioning as an electrode and a mask are deposited by evaporation at the same time on the whole surface of an Si photo diode, and a part of it is trimmed (by etching) to make up the light-receiving surface 8, thereby reducing the sensitivity of the photo-detector 2. A sectional view of the photo-detector 2 is shown in FIG. 3. In this way, the width of the slit 4 can be increased. Also, the change in the sensitivity of the photo-detector 2 is reduced as compared with the change in the slit width, thus facilitating the adjustment.

Figure 4:
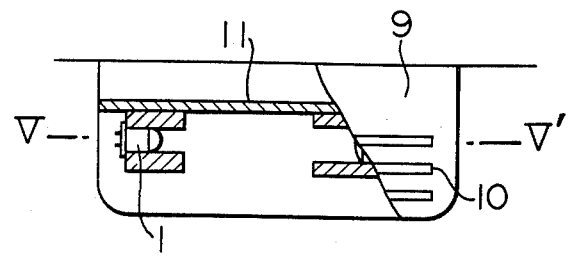
FIGS. 4 and 5 are a partly-cutaway front sectional view of a smoke detector according to the present invention and a sectional view taken along the line V—V' thereof respectively.
Figure 5:
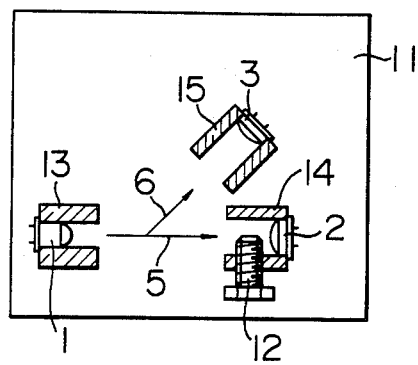

FIG. 4 shows a longitudinal sectional view of a specific configuration of a photo-electric smoke detector according to the present invention, and FIG. 5 a longitudinal sectional view along line V—V' in FIG. 4. Numeral 9 designates a smoke detector proper of a construction adapted to be mounted on the ceiling of the interior of a car. Slits 10 providing a smoke entrance are formed in the side wall and the lower side of the detector. Numeral 1 designates an infrared light-emitting diode (hereinafter referred to as LED), numeral 2 an Si photo-diode (hereinafter referred to as SiPD) for receiving direct light from the light source 1, and numeral 3 an SiPD for receiving light scattered by smoke. Both the SiPDs are secured to a base plate by fittings 13, 14, 15. A screw 12 for regulating the amount of light entering SiPD 2 is provided forwardly of SiPD 2.

Figure 2:
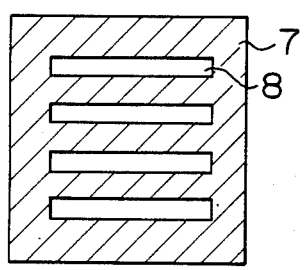
FIGS. 2 and 3 are front and sectional views of a second photo-detector respectively.
Figure 6:
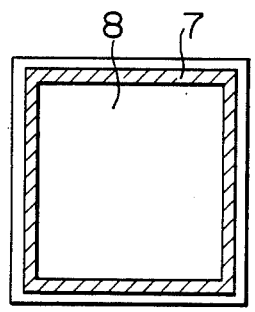
FIGS. 6 and 7 are front and sectional views respectively of a first photo-detector.
Figure 7:
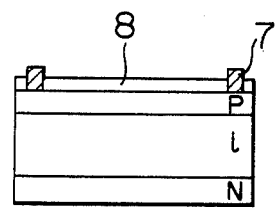

SiPD 2 is integrated with the metal member 7 shown in and described with reference to FIGS. 2 and 3 above. SiPD 3, on the other hand, has a construction shown in FIG. 6 (front view) and FIG. 7 (sectional view). These SiPDs are fabricated in the same processes as an ordinary SiPD of PIN type. The difference between SiPD 2 and SiPD 3 lies in the shape of the electrode 7 on P layer side made of Al or Av.

SiPD 3 is constructed of the light-receiving surface 8 for the most part thereof, while the greater part of SiPD 2 is covered with the electrode 7. SiPD 2, which receives only the light entered by way of the light-receiving surface in the form of slits, is lower than SiPD 3 in sensitivity.

SiPDs 2 and 3, which are different only in the shape of the electrode 7, have exactly the same temperature characteristic and frequency response, and are therefore used advantageously against temperature changes or modulated light.

Figure 8:
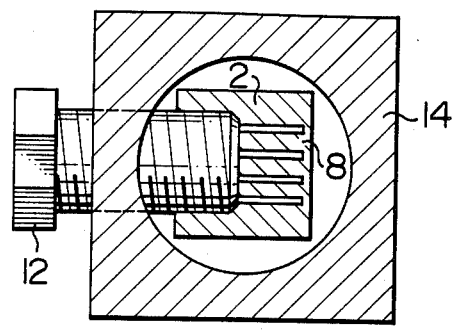
FIG. 8 is a diagram showing a regulating system of the second photo-detector.

SiPD 2, as shown in FIG. 8, is mounted on the fitting 14 in such a manner that the longitudinal direction of the light-receiving surface 8 in slits concides with the direction of driving the screw 12. In this mounting position, the output of the SiPD 2 is changed linearly with the movement of the screw thereby to secure accurate adjustment.

Figure 9:
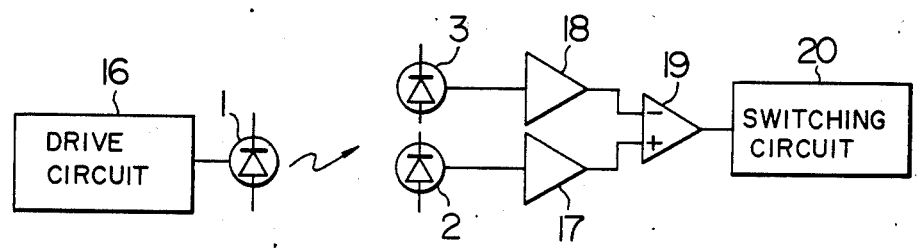
FIG. 9 shows an electrical circuit.

A block diagram of the detector circuit of the smoke detector is shown in FIG. 9. Numeral 16 designates a drive circuit for causing LED 1 to emit light, numeral 17 an amplifier circuit for SiPD 2, numeral 18 an amplifier circuit for SiPD 3, numeral 19 a comparator, and numeral 20 a switching circuit operated in response to signals from the comparator 19.

The operation of the first embodiment will be described below. In the absence of smoke, the light emitted from LED 1 enters SiPD 2 while part of the light is reflected on the inner wall or like of the detector 9 and is applied to SiPD 3. If the amount of light which enters SiPD 2 is adjusted to make the outputs of the amplifiers 17 and 18 equal to each other, under this condition, the detector is not actuated as the comparator 19 is not operated. According to the present invention, SiPD 2 is lower in sensitivity than SiPD 3, and therefore the amount of change in the output of SiPD 2 is small as compared with the amount of feed of the screw 12 for adjusting the amount of light, thus greatly facilitating the adjustment. Further, the adverse effect of movement of the screw by vibrations of the car is minimized.

Now assume that cigarette smoke or like flows into the detector through the slits 10. The light 6 scattered by the smoke enters SiPD 3, so that the output of the amplifier 18 exceeds the output of the amplifier 17, thus activating the comparator 19 thereby to start the detector.

Figure 10:
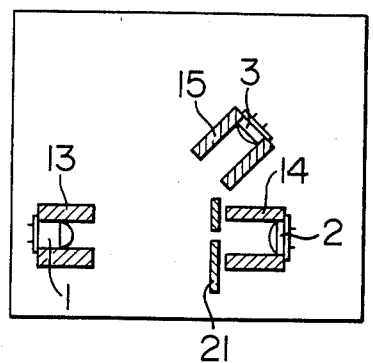
FIGS. 10 and 11 are a sectional view of another embodiment of the present invention and an enlarged view of the essential parts thereof.
Figure 11:
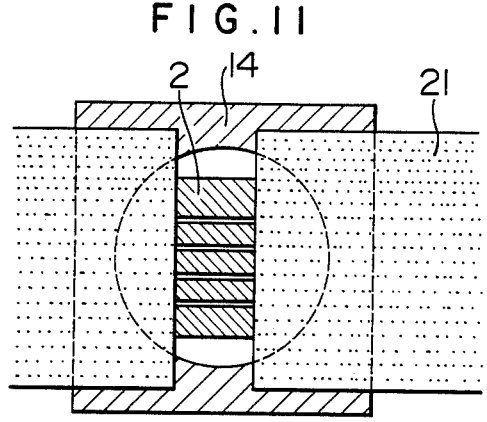

A sectional view of a second embodiment of the present invention is shown in FIG. 10. LED 1, SiPD 2 and SiPD 3 are equivalent to those included in the first embodiment.

Slits 21 are formed before SiPD 2 to make sure that the longitudinal direction of the light-receiving surface 8 in slits is identical to the direction of opening and closing of the slits 21 by which the amount of light entering SiPD 2 is regulated.

The operation of the detector in this case is quite the same as that of the first embodiment.

Figure 12:
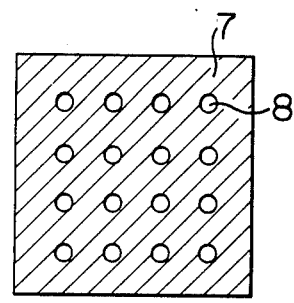
FIG. 12 is a front view of the second photo-detector according to still another embodiment of the present invention.

A third embodiment of the present invention will be explained. The SiPD 2 of a construction as shown in FIG. 12 is used in the third embodiment. Specifically, small holes are formed as the light-receiving surface 8, and the remaining parts are covered fully by the metal member 7. Also in this case, only the light entering by way of the parts 8 lacking the metal member 7 is detected and therefore the sensitivity is reduced. This SiPD may be used in quite the same way as those of the first and second embodiments. If the holes are arranged densely along the direction of screw feed or the direction in which the slit width is changed, the output of SiPD changes almost linearly with the slit width, thereby facilitating adjustment.

It will thus be understood from the foregoing description that according to the present invention, there is provided a smoke detector in which part of the electrode of the photo-detector for receiving direct light is trimmed in order to reduce the sensitivity thereof, and therefore the means for reducing the sensitivity can be integrated with the photo-detector, so that the detection capacity is prevented from deteriorating by vibrations or like.

We claim:

1. A photo-electric detector comprising:
   a light emitter;
   first light receiver means for receiving light directly from said light emitter;
   said first light receiver means having a light suppression film integrally provided on a light receiving surface thereof for suppressing an amount of said light received by the light receiving surface;
   said light suppression film being made of a metal material which also forms at least a portion of an electrode of said first light receiver means;
   light adjusting means, provided in proximity to the receiving surface of said light receiver for varying a lateral area of said light received by said light receiving surface and said light suppression film by an adjustment thereof; and
   second light receiver means for receiving reflected light from said light emitter.

2. A photoelectric detector as in claim 1 further comprising means for comparing an output of said first light receiver means indicative of an amount of light received thereby with an output of said second light receiver means indicative of an amount of light received thereby.

3. An apparatus as in claim 2 further comprising switching means for signaling an alarm when said output of said second light receiver means becomes higher than said output of said first light receiver means.

4. A photoelectric smoke detector comprising:
   a chamber defining a flow path for smoke;
   light emitting means provided in said chamber;
   first light receiving means arranged at a predetermined angle relative to said light emitting means, for receiving only a scattered light;
   second light receiving means arranged in line with said light emitting means, for receiving light directly therefrom;
   regulation means for regulating an amount of light incident on said second light receiving means; and
   said second light receiving means having an electrode acting as a light shielding member for shielding only a part of a light receiving surface thereof, said second light receiving means having a light shielded area, which is larger than a light shielded area of said first light receiving means, and having a light sensitivity of which is smaller than a light sensitivity of said first light receiving means.

5. A photoelectric smoke detector according to claim 4 wherein:
   the electrode of said second light receiving means is made of aluminum or gold and has a number of elongate rectangular windows formed therein and arranged side by side.

6. A photoelectric smoke detector according to claim 4 wherein:
   the electrode of said second light receiving means has a plurality of small holes formed therein and arranged in matrix array.

7. An apparatus as in claim 4 further comprising comparator means for comparing an output of said first light receiving means indicative of an amount of scattered light received thereby with an output of said second light receiving means indicative of an amount of direct light received thereby, and producing an output indicative thereof.

8. An apparatus as in claim 7 further comprising switching means coupled to said output of said comparator means, for signaling an alarm condition when said output of said comparator means indicates that said first light receiving means has received an amount of light more than said second light receiving means.

* * * * *